(12) United States Patent
Yan et al.

(10) Patent No.: US 8,342,030 B1
(45) Date of Patent: Jan. 1, 2013

(54) APPARATUS FOR DEFORMING FIBRES

(75) Inventors: Dongbo Yan, Fredericton (CA);
Kecheng Li, Fredericton (CA)

(73) Assignee: University of New Brunswick,
Fredericton, New Brunswick ( * ) Notice: Subject to any disclaimer, the term of this patent is extended or adjusted under 35 U.S.C. 154(b) by 0 days.

(21) Appl. No.: 12/910,444

(22) Filed: Oct. 22, 2010

(51) Int. Cl.
*G01L 7/08* (2006.01)

(52) U.S. Cl. .......................................... 73/715; 382/111

(58) Field of Classification Search ............. 73/700–756
See application file for complete search history.

(56) References Cited

U.S. PATENT DOCUMENTS

| | | | |
|---|---|---|---|
| 4,253,329 A | | 3/1981 | Karnis |
| 5,331,405 A | | 7/1994 | Fransson et al. |
| 5,438,876 A | * | 8/1995 | Lewis ............... 73/726 |
| 5,481,919 A | * | 1/1996 | Brandt, Jr. ........ 73/723 |
| 6,432,272 B1 | * | 8/2002 | Hollenberg et al. ..... 162/204 |
| 2009/0279743 A1 | * | 11/2009 | Li et al. ............. 382/111 |
| 2010/0028999 A1 | * | 2/2010 | Nain ................ 435/377 |

FOREIGN PATENT DOCUMENTS

| | | |
|---|---|---|
| CA | 1115552 | 1/1982 |
| CA | 2069508 | 9/1991 |

OTHER PUBLICATIONS

Nilsson, B., Lars Wågberg and Gray, D., "Conformability of wet pulp fibres at small Length Scales". 12th Fundamental Research Symposium, p. 211 (2001).

Samuelsson, L.G., "Measurement of the stiffness of fibres". Svensk. Papperstidn 15(1):S41-S46 (1963).
Mohlin, U-K., "Cellulose fibre bonding Part 5: Conformability of pulp fibres". Svensk. Papperstidn 78(11):412-416 (1975).
Kerekes, R.J. and Tam Doo, P.A., "Wet fibre flexibility of some major softwood species pulped by various processes". J. Pulp Paper Sci. 11:60-61 (1985).
Kuhn, D.C.S., Lu, X., Olson, J.A. And Robertson, A.G., "Dynamic wet fibre flexibility measurement device". J. Pulp Paper Sci. 21(1):337 (1995).
Steadman, R. and Luner, P., "The effect of wet fibre flexibility of sheet apparent density ". 8th Fundamental Research Symposium p. 211 (1981).
Seborg, C.O. and Simmonds, F.A., "Measurement of stiffness in bending of single fibres". Paper Trade Journal 113(1):49-50 (1941).
James, W.L., A method for studying the stiffness and internal friction of individual fibres. Wood Sci. 6(1):30-38 (1973).
Tam Doo, P. A. and Kerekes, R.J., "Method to measure wet fibre flexibility". Tappi 64:113-116 (1981).
Zhang, M., Hubbe, M.A., Venditti, R.A. and Heitmann, J.A., "Effects of sugar addition before drying on the wet flexibility of redispersed kraft fibres". J. Pulp Paper Sci. 30:29-34 (2004).

(Continued)

*Primary Examiner* — Andre Allen
(74) *Attorney, Agent, or Firm* — Eugene F. Derényi; Fogler, Rubinoff LLP

(57) ABSTRACT

An apparatus comprising a housing comprising an end wall and side walls defining a first chamber open at one end a slide at the open end a diaphragm in the chamber spaced from the slide and generally parallel to it, defining, with the slide and side walls of the first chamber, a second chamber; and an opening in the first chamber for permitting fluid to enter and exit the first chamber.

12 Claims, 4 Drawing Sheets

OTHER PUBLICATIONS

Delgado, E., Lopez-Dellamary, F.A., Allan, G.G., Andrade, A., Contreras, H., Regla, H. and Cresson, T., "Zwitterion modification of fibres: Effect of fibre flexibility on wet strength of paper". J. Pulp Paper Sci. 30:141-144 (2004).

Karnis, A., "Mechanism of fibre development in mechanical pulping". J. Pulp Paper Sci. 20(1):280-288 (1994).

Jang, H. F., "A Theory for the Transverse Collapse of Wood Pulp Fibres", 12th Fundamental Research Symposium, Oxford, Sep. 2001.

* cited by examiner

APPARATUS FOR DEFORMING FIBRES

FIELD

The present application relates to apparatus for deforming fibres in general and deforming fibres for measuring of fibre flexibility in particular.

BACKGROUND

Modern paper and paper board is predominantly composed of a matrix of wood fibres. During the consolidation stage of papermaking, individual wet fibres are drawn and entangled together, forming a web structure. The deformability of the wet fibres used is a significant measure of the ability of the fibres to conform to each other by providing bonding contact in the course of dewatering, pressing, and drying. Fibre flexibility is a significant measure of fibre deformability. Fibres which are flexible are more conformable to one another, thus forming more contact area among fibres.

Fibre flexibility determines the total inter-fibre contact area and the voids in the fibre network, and plays a dominant role in determining most paper properties, such as bulk, permeability, opacity, surface smoothness, and physical strength. There are several prior art apparatus and methods for measuring the flexibility of individual wet fibres.

The measurement of single fibre elastic modulus is usually performed by micro-tensile testing. The difficulties associated with this test are the dimensions of individual wood fibres, which are short (1-5 mm) and thin (10-30 um in diameter) and require careful handling and mounting techniques in sample preparation, and accurate measurements for stress and strain in a very small scale [1]. Because of the heterogeneous nature, a large population of fibres needs to be tested for the statistical analysis. Tedious and time-consuming operations in the fibre scale become a major drawback of this test method and make it impractical for engineering applications.

Some existing prior art methods treat the fibre as a cantilever [2-6]. Most of these methods are based on small deflection beam theory, which involves measuring the displacement of a fibre beam when applying a transverse force or bending moment on the fibre. If the fibre is treated as a beam subject to pure elastic deformation, the flexibility (F) of individual fibres can be defined as the reciprocal of its bending (also sometimes referred to as flexural stiffness) EI, where E is the elastic modulus of the fibre wall and I is the moment of inertia of the fibre cross-section: $F=1/EI$.

Seborg and Simmonds [8], for example, measured the stiffness of dry fibres by clamping individual fibres into place and then exerting a force on a fibre using a quartz spring to bend it like a cantilever beam. The flexural stiffness EI is determined from the slope of the load-deflection curve. The test suffers from two main disadvantages: (1) it is done on single fibres, making it very tedious and cumbersome; and (2) the clamping can damage the fibre.

James [8] calculated the fibre stiffness by measuring the resonance frequency of a fibre cantilever. Hydrodynamic or bending beam methods have also been developed for the fibre flexibility measurement by hydrodynamic forces generated by water flow and image analysis, so that individual fibre handling can be avoided.

Various apparatus have been developed for supporting the fibres. For example, Samuelsson [2] used a mechanical jaw to clamp fibres. Tam Doo and Kerekes [9] supported fibre on one end of a capillary tube so that mechanical damage to the fibre can be avoided. Like the Seborg and Simmonds method, the Tam Doo and Kerekes method is limited to testing individual fibres.

Kuhn et al. [5] developed a device that bends fibres by a T-junction tube when fibres in water flow out of a capillary. The fibre deformation is observed by a microscope and the force is calculated according to hydrodynamic theory. The Kuhn method is a direct measure of the flexibility of a fibre and may give flexibility results that are higher than expected [5].

Conformability testing as opposed to directly measuring flexibility is another typical method for fibre flexibility measurement. This method was first proposed by Mohlin [3]. In this method, wet pulp fibres are deposited onto a thin glass fibre (diameter=60 μm) that is fixed on a glass slide. The wet fibre arcs over the glass fibre and then is allowed to dry. The non-contact span, or freespan, length of the fibre is determined to calculate the fibre flexibility according to the beam deflection theory. Since only a conventional light microscope is required, and it can provide a numerical measure in an engineering unit, this method has commonly been used for fibre flexibility measurement [10-12]. No pressure, however, is applied to the fibre when taking the measurement and most likely does not approximate what happens in a paper structure of such fibres.

Steadman and Luner [6] have sought to improve upon the Mohlin method by taking the advantage that it does not need to handle individual fibres. In the Steadman method, a wire of 25 μm diameter was used as the support wire for forming the fibre arc over it.

In the Steadman method, fibres are deposited on a filter paper and wet pressed onto a thin support wire that is fixed on a glass slide. The fibre and the support wire are approximately 90 degrees to one another such that when pressed onto the wire, the fibre is subjected to a uniform distributed load and forms an arch-like span over the wire as it deforms. The fibre is then allowed to dry and the sections of the fibre in contact with the slide become adhered to the glass slide. The length of the section of the span not in contact with the glass slide, referred to as the non-contact span or freespan length, is measured from above using a conventional light microscope with incident lights, under which the optical contact zone of the fibre and the glass slide appears in dark, whereas the non-contact zone appears in light, thus the freespan length is measured. The freespan length measurement is then used in the calculation of flexibility according to the following formula:

$$F=1/EI=72d/PWS^4$$

Where E=modulus of elasticity ($Nm^{-2}$)
I=moment of inertia ($m^4$)
d=wire diameter (m)
P=pressing pressure ($Nm^{-2}$)
W=projected fibre width (m)
S=mathematical estimate of the loaded span (m)

There are two important assumptions implied with this method: 1) the bonding strength between fibre and glass slide surface are high enough thus fibres are bonded on the glass slide at any place where they come into contact; 2) the freespan length of fibres remain unchanged while fibres are getting dried and after the pressure load is released. In practice, the fibre-glass surface bonding strength is not always sufficient to fix fibre on the glass slide, particularly for mechanical pulp fibres and unrefined chemical pulp fibres, which have much lower bonding strength compared with well refined chemical pulp fibres. Fibres that have high stiffness (low flexibility) have a higher tendency to spring back when external press load is removed, resulting in larger freespan or even totally becoming unbounded from the glass slide. For fibres that have low stiffness (high flexibility), the shape of the fibres arcing over the support can also be altered by the high surface tension while drying. All of these lead to an inaccurate measurement or are unable to conduct measurement for fibres that either have high stiffness and low bonding strength or have higher flexibility.

SUMMARY

The invention in one aspect relates to an apparatus comprising a housing comprising an end wall and side walls defining a first chamber and having an opening at one end; a diaphragm and a slide spanning the opening of the chamber wherein the diaphragm is located on the chamber side of the slide. The diaphragm can hermetically seal the opening. The first chamber can have an opening for permitting fluid to enter and exit the first chamber. The diaphragm is flexible from relaxed position and a flexed position wherein the diaphragm is biased toward the slide. The slide can be in partial contact with the diaphragm and together with the slide can define a second chamber into which a wire and fibre samples to be tested can be placed.

The invention, in one aspect, relates to an apparatus for deforming a wet fibre without handling the individual fibre. The invention, in another aspect, relates to an apparatus comprising a housing comprising an end wall and side walls defining a first chamber open at one end; a slide at the open end; a diaphragm in the chamber spaced from the slide and generally parallel to it, defining, with the slide and side walls of the first chamber, a second chamber; and an opening in the first chamber for permitting fluid to enter and exit the first chamber.

According to another aspect, the invention relates to an apparatus comprising: a housing comprising an end wall and side walls defining a first chamber open at one end; a glass slide with glass wires fixed on at the open end; a diaphragm in the chamber spaced from the slide and generally parallel to it, defining, with the slide and side walls of the first chamber, a second chamber; an opening in the first chamber for permitting fluid to enter and exit the first chamber; a regulator for adjusting the pressure; a three-way valve directing fluid into the chamber and releasing the pressure; and a pressure gauge for measuring the pressure while pressing.

DETAILED DESCRIPTION OF THE INVENTION

According to one embodiment, the present invention relates to an apparatus for deforming wet pulp fibre in order to observe the shape of the wet fibres while they are subjected to a known pressing pressure. Measurements of various dimensions of the fibres can then be made using optical section images or image series and calculating the flexibility, moment of inertia, and in turn, the elastic modulus of the fibre wall.

Figure 1:
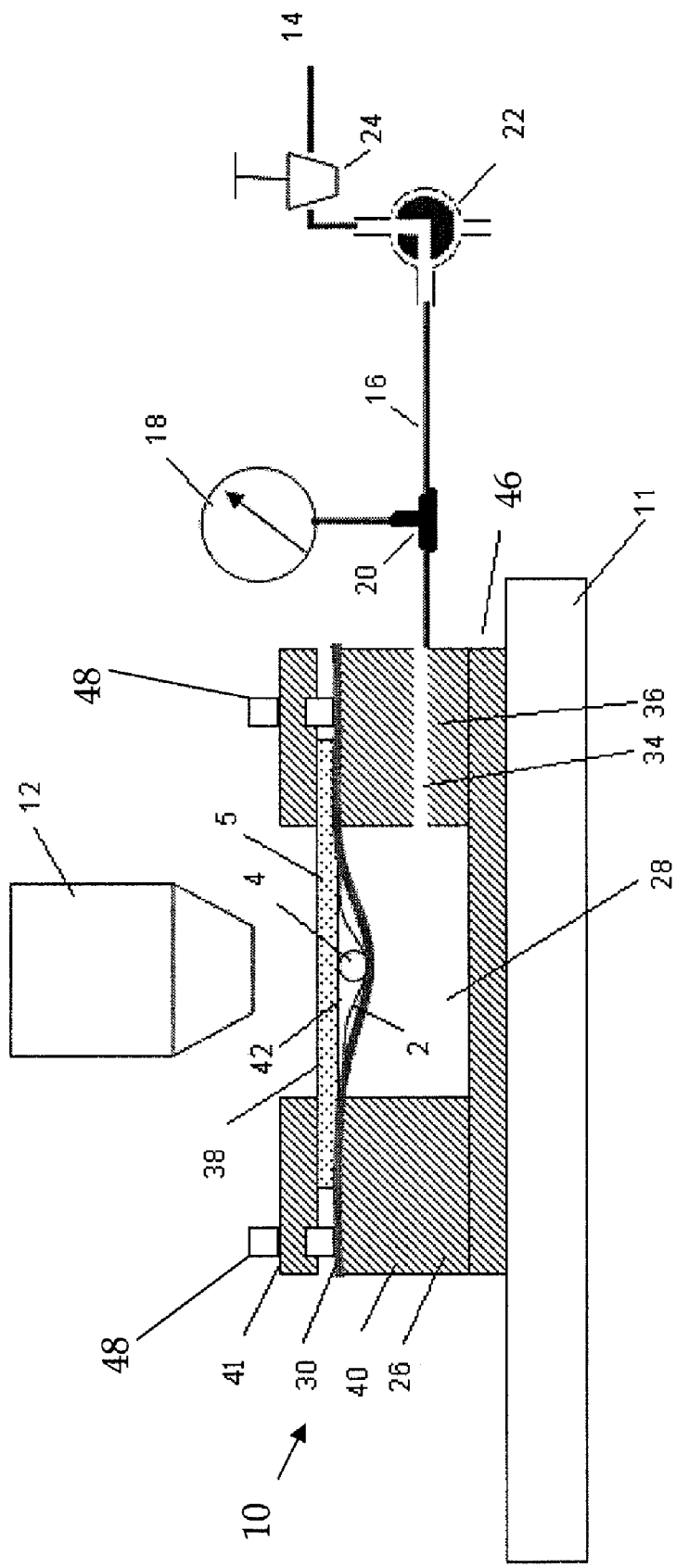
FIG. 1 is a schematic drawing of a set-up with an apparatus according to one embodiment of the present invention.

Referring initially to FIG. 1, an embodiment of an apparatus according to the invention is indicated generally at 10 and is used to hold a fibre sample for observation under a conventional microscope or a CLSM 12. As is described more fully below, the apparatus 10 is operated by fluid (a gas or a liquid) pressure and is connected to a fluid pressure source 14 by line 16. Situated on the line 16 between the source 14 and the apparatus 10 is a pressure gauge 18 which is connected to line 16 by T-connector 20, three-way valve 22 and fluid pressure regulator 24.

The apparatus 10 is designed to fit on the stage 11 of microscope 12. Apparatus 10 comprises a housing 26 having a base 46 and sidewalls 36 which define a chamber 28 which is open at the top. A diaphragm 30 hermetically seals the open top of the chamber 28. The diaphragm 30 is made of soft and flexible non-fluorescent rubber or other suitable material. A microscope slide 38 is located over the diaphragm 30 such that at least the edges of the diaphragm 30 are sandwiched between the slide 38 and the tops of the side walls 36 and end walls 44 and is held in place. A removable cover plate 41 having a central opening is located on the slide 38. The plate 41 is held in place by screws 48 which are received in bores 50 in the housing 26. The opening in plate 41 permits optical access to the slide 38. A fluid passageway 34 is provided in one of the sidewalls 36 of the housing 26 to permit fluid to enter (from fluid pressure source 14) and be evacuated from the chamber 28.

Figure 2:
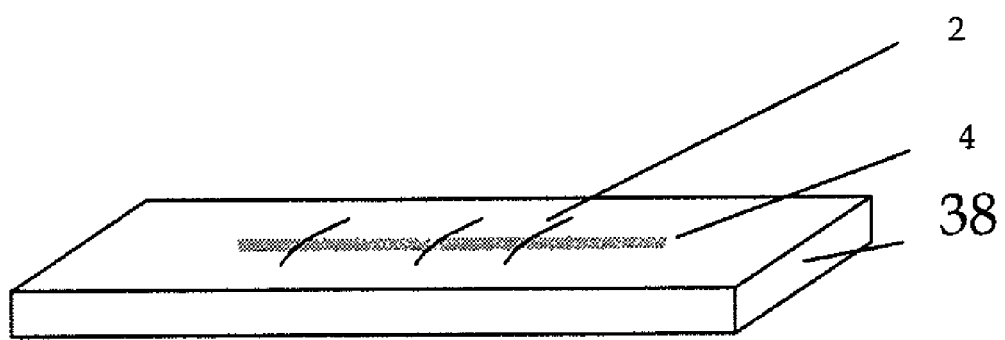
FIG. 2 is a schematic of a glass wire being prepared for mounting on a glass slide according to the present invention.
Figure 3:
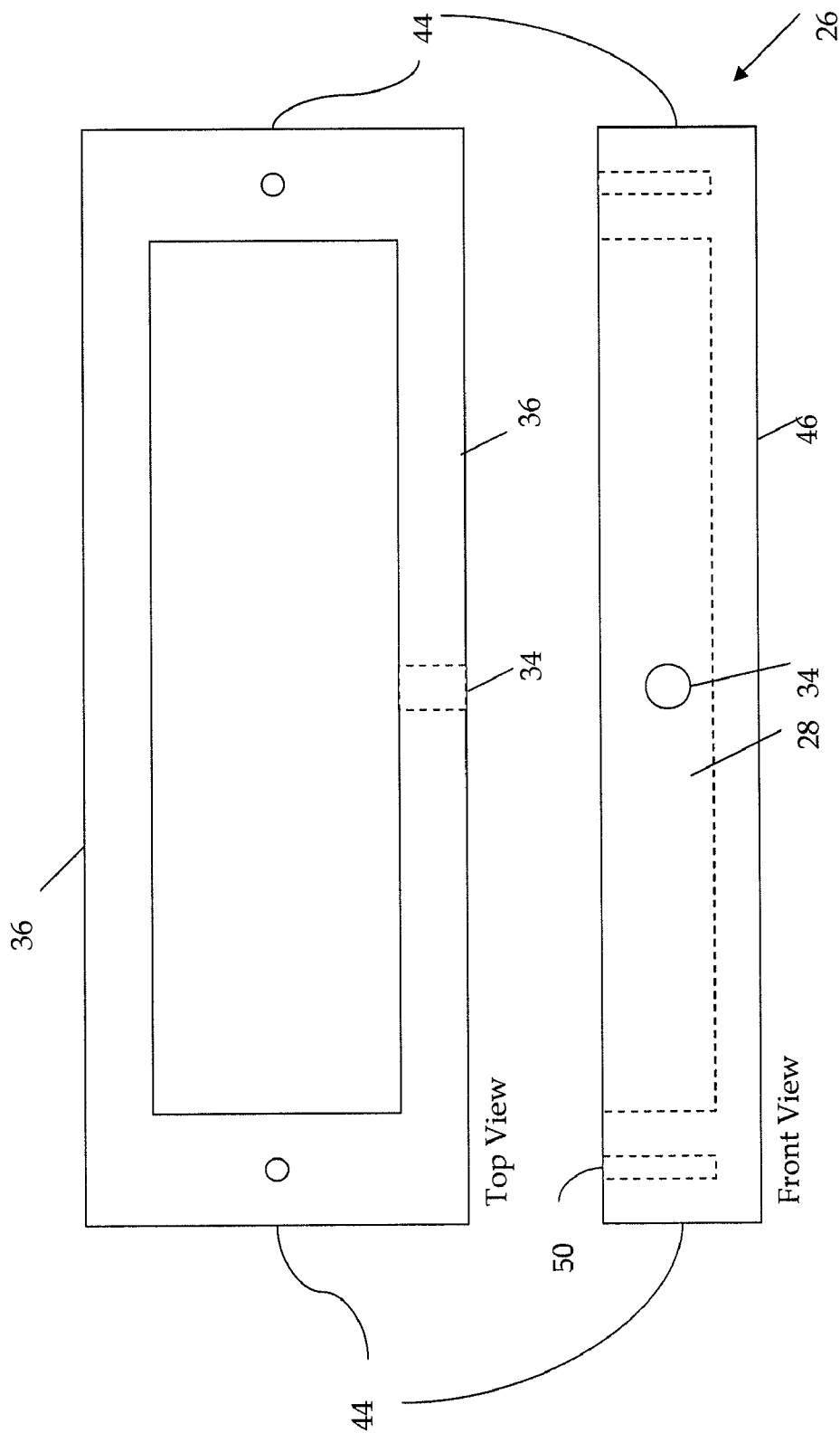
FIG. 3 is a top and side view of a housing according to one or more embodiments of the present invention.
Figure 4:
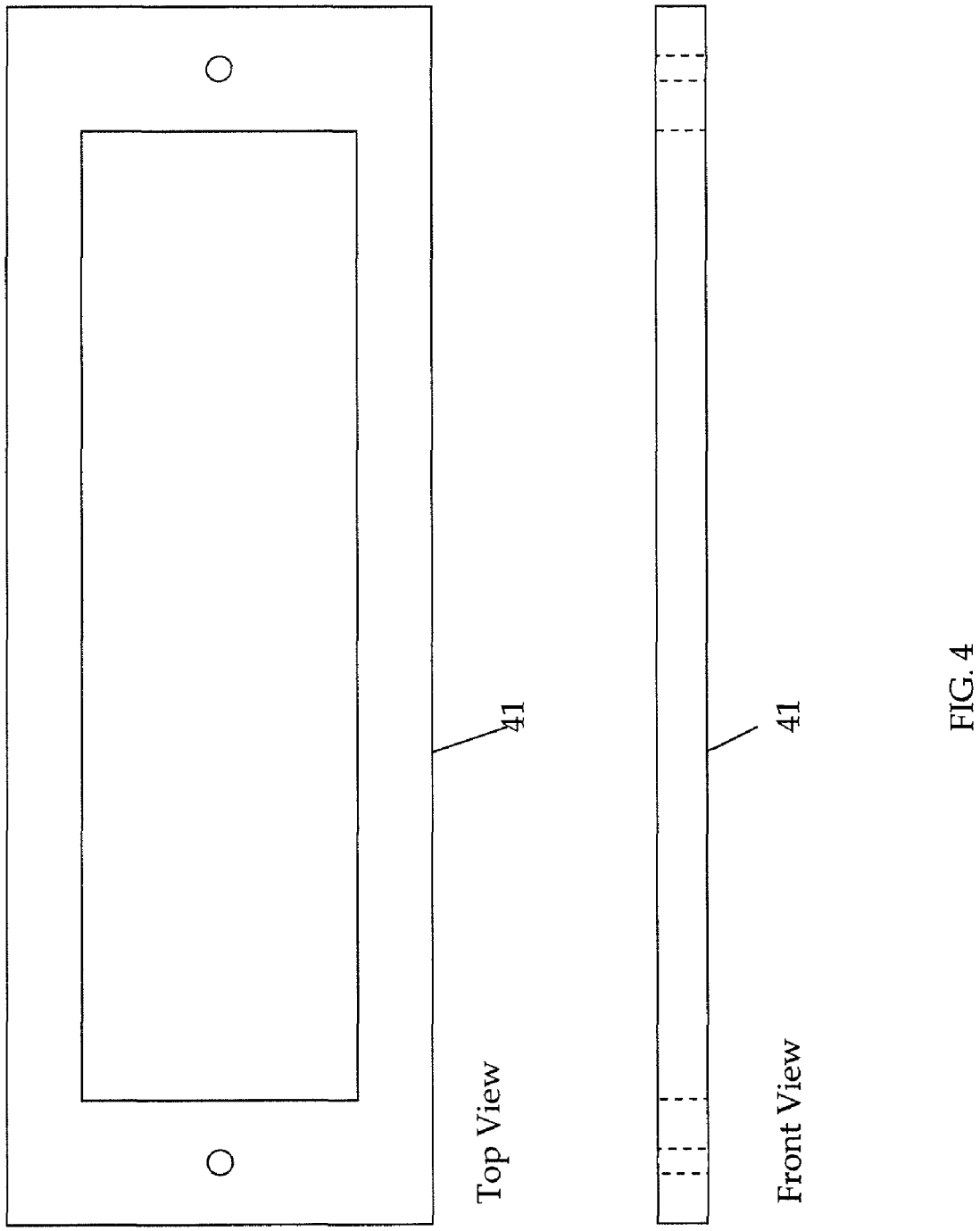
FIG. 4 is a top and side view of a cover plate according to one or more embodiments of the present invention.

In operation, in one embodiment of the present invention, fibres are prepared for observation in a manner similar to the set-up method used in the Steadman method. A glass support wire 4 with a diameter of about 10 um is fixed on a microscope glass slide 38 with an adhesive suitable for glass such as nail polish. The glass wire 4 of known diameter serves as the support for the fibres 2 in the same way as the support wire in the Steadman method. Pulp fibres 2 are stained with a suitable fluorescent dye and suspended in water. The fibre suspension (not shown) is swirled and then drained through a filter paper (not shown) and the pulp fibres 2 are deposited on the filter paper (not shown). The pulp fibres 2 with the filter paper are then placed onto the glass wire 4 and the glass slide 38. Blotting paper (not shown) is used to absorb excess free water by gently pressing the blotting paper on the back of the filter paper. Then the blotting paper and filter paper are removed in such a way that the fibres 2 to be measured are "left behind" and thereby transferred to the glass slide 38 as shown in FIG. 2. At least some of the fibres 2 should be positioned spanning the glass wire 4 at a substantially perpendicular angle to the glass wire 4. The prepared slide 38 is then inverted and placed in the apparatus 10 between the diaphragm 30 and the plate 41 as shown in FIG. 1. The apparatus 10 is placed on the stage 11 of a microscope 12 (with only objective lens shown).

The fluid pressure in chamber 28 is gradually increased to a desired value, which is indicated by the gauge 18. The pressure in the chamber 28 presses the diaphragm 30 against the slide 38 and the fibres 2 and the wire 4 whereby the fibres 2 deform around the wire 4. Fibres 2 to be analysed and a glass wire 4 with known diameter are placed in the sample chamber 42. If observation of the fibres 2 while wet is desired, water or other fluid can be placed in the sample chamber 42. The pressure in the chamber 28 is then increased by introducing a fluid under pressure via the passageway 34 into the chamber 28. As the fluid pressure in the chamber 28 increases, pressure is exerted against the diaphragm 30 until the diaphragm 30 is flexed toward the slide 38, pressing the fibres 2 against the wire 4 such that it deforms (arcs) around the glass wire 4 as seen in FIG. 2. The fibres 2 can then be observed in the deformed state and measurements taken (such as the measurements described above for calculating the flexibility of the fibre). Fluid is evacuated from the chamber 28 to relax the diaphragm 30.

The pressure exerted against by the diaphragm 30 against the slide 38 should not exceed the strength of the slide 38, to avoid breaking it. The fluid pressure can be monitored with the pressure gauge 18 and regulated as needed with the pressure regulator 24.

For fibre flexibility measurements, the freespan length (L) and the deflection height (d) are measured. The freespan length is the length along the x-axis of the non-contact section of the fibre span i.e. the section not in contact with the glass slide. The freespan length is L1 and L2 and the deflection height is d, which is the diameter of the glass fibre 4. The deflection height d can also be obtained from XZ section images directly from the CLSM.

A CLSM is then used to image the fibres 2. The basic imaging mode of CLSM is an XY plane or section of the sample of the focal plane. The major difference between CLSM and conventional LM is that CLSM allows only the signals from the focal plane to be recorded, so the image formed is only a plane, not the entire sample object. By changing the focal plane along the height direction, a series of focal planes, also called optical sections, can be imaged. Free span lengths (L1, L2) then can be measured accordingly.

A cross-section of the fibre can be obtained by operating the CLSM in XY scan mode and scanning perpendicular to the fibre axial from which the fibre width (w) and the moment of inertia (I) are measured and calculated.

An alternative microscopic method for fibre flexibility measurements can also be used by equipping a reflectance light microscope with a vertical (Z) scanner, not shown in FIG. 1. A series of images of fibre surfaces are taken at a different Z position, and the 3D shape of deformed fibre is reconstructed by finding all points at the focal plane of each image of the series. The 3D shape of the fibre is calculated. The L1 and L2 then are measured from the 3D images for calculating fibre flexibility. Fibre flexibility measurements can also be conducted on a fibre or fibres deformed using an apparatus according to the invention, using the methods described in applicants' U.S. patent application Ser. No. 12/116,012 which is incorporated herein by reference in its entirety.

The following references are referred to in this application and are incorporated herein by reference:
1. NILSSON, B., LARS WÅGBERG and GRAY, D., "Conformability of wet pulp fibres at small Length Scales". 12th Fundamental Research Symposium, p. 211 (2001)
2. SAMUELSSON, L. G., "Measurement of the stiffness of fibres". Svensk. Papperstidn 15(1):S41-S46 (1963)
3. MOHLIN, U-K., "Cellulose fibre bonding Part 5: Conformability of pulp fibres". Svensk. Papperstidn 78(11): 412-416 (1975)
4. KEREKES, R. J. and TAM DOO, P. A., "Wet fibre flexibility of some major softwood species pulped by various processes". J. Pulp Paper Sci. 11:60-61 (1985)
5. KUHN, D. C. S., LU, X., OLSON, J. A. and ROBERTSON, A. G., "Dynamic wet fibre flexibility measurement device". J. Pulp Paper Sci. 21(1):337 (1995)
6. STEADMAN, R. and LUNER, P., "The effect of wet fibre flexibility of sheet apparent density". 8th Fundamental Research Symposium p. 211 (1981)
7. SEBORG, C. O. and SIMMONDS, F. A., "Measurement of stiffness in bending of single fibres". Paper Trade Journal 113(1):49-50 (1941)
8. JAMES, W. L., "A method for studying the stiffness and internal friction of individual fibres. Wood Sci. 6(1):30-38 (1973)
9. TAM DOO, P. A. and KEREKES, R. J., "Method to measure wet fibre flexibility". Tappi 64:113-116 (1981)
10. ZHANG, M., HUBBE, M. A., VENDITTI, R. A. and HEITMANN, J. A., "Effects of sugar addition before drying on the wet flexibility of redispersed kraft fibres". J. Pulp Paper Sci. 30:29-34 (2004)
11. DELGADO, E., LOPEZ-DELLAMARY, F. A., ALLAN, G. G., ANDRADE, A., CONTRERAS, H., REGLA, H. and CRESSON, T., "Zwitterion modification of fibres: Effect of fibre flexibility on wet strength of paper". J. Pulp Paper Sci. 30:141-144 (2004)
12. KARNIS, A., "Mechanism of fibre development in mechanical pulping". J. Pulp Paper Sci. 20(1):280-288 (1994)

We claim:

1. An apparatus comprising:
a housing comprising an end wall and side walls defining a first chamber and having an opening at one end;
a diaphragm and a slide spanning the opening of the chamber wherein the diaphragm is located on the chamber side of the slide.

2. The apparatus of claim 1 wherein the diaphragm hermetically seals the opening.

3. The apparatus of claim 2 further comprising an opening in the first chamber for permitting fluid to enter and exit the first chamber.

4. The apparatus of claim 2 wherein the diaphragm is flexible from relaxed position and a flexed position wherein the diaphragm is biased toward the slide. further comprising a liquid in the second chamber.

5. The apparatus of claim 1 wherein the slide is in partial contact with the diaphragm and together with the slide define a second chamber.

6. The apparatus of claim 5 further comprising a wire in the second chamber.

7. The apparatus of claim 6 wherein the wire is adhered to the diaphragm side of the slide.

8. The apparatus of claim 5 wherein the slide is transparent.

9. The apparatus of claim 3 further comprising a fluid pressure source in fluid communication with the first chamber.

10. The apparatus of claim 9 further comprising a pressure regulator in fluid communication with the fluid pressure source.

11. The apparatus of claim 10 further comprising a pressure gauge in fluid communication with the fluid from the fluid pressure source.

12. The apparatus of claim 11 further comprising a microscope.

* * * * *